United States Patent
Kompaniets et al.

(10) Patent No.: US 11,679,293 B2
(45) Date of Patent: Jun. 20, 2023

(54) QUARTERNARY AMMONIUM HALIDES FOR TREATING HALOGEN CONTAMINATION

(71) Applicant: BROMINE COMPOUNDS LTD., Beer-Sheva (IL)

(72) Inventors: Igor Kompaniets, Beer Sheva (IL); Or Press Frimet, Lehavim (IL); Ofer Cohen, Omer (IL); Ran Elazari, Kibbutz Mishmar Hanegev (IL)

(73) Assignee: BROMINE COMPOUNDS LTD., Beer-Sheva (IL)

( * ) Notice: Subject to any disclaimer, the term of this patent is extended or adjusted under 35 U.S.C. 154(b) by 0 days.

(21) Appl. No.: 17/614,425

(22) PCT Filed: May 27, 2020

(86) PCT No.: PCT/IL2020/050593
§ 371 (c)(1),
(2) Date: Nov. 26, 2021

(87) PCT Pub. No.: WO2020/240561
PCT Pub. Date: Dec. 3, 2020

(65) Prior Publication Data
US 2022/0226685 A1 Jul. 21, 2022

Related U.S. Application Data

(60) Provisional application No. 62/853,177, filed on May 28, 2019.

(51) Int. Cl.
| | | |
|---|---|---|
| A62D 3/33 | (2007.01) |
| A62D 3/37 | (2007.01) |
| B01D 53/68 | (2006.01) |
| C07C 211/63 | (2006.01) |
| C07D 213/20 | (2006.01) |
| A62D 101/49 | (2007.01) |

(52) U.S. Cl.
CPC ............... *A62D 3/33* (2013.01); *A62D 3/37* (2013.01); *B01D 53/68* (2013.01); *C07C 211/63* (2013.01); *C07D 213/20* (2013.01); *A62D 2101/49* (2013.01); *B01D 2251/206* (2013.01); *B01D 2251/304* (2013.01); *B01D 2251/404* (2013.01); *B01D 2251/80* (2013.01); *B01D 2257/2022* (2013.01); *B01D 2257/2025* (2013.01)

(58) Field of Classification Search
CPC ........ A62D 3/33; A62D 3/37; A62D 2101/49; B01D 53/68; B01D 2251/206; B01D 2251/304; B01D 2251/404; B01D 2251/80; B01D 2257/2022; B01D 2257/2025; B01D 2257/02; B01D 2257/202; C07C 211/63; C07C 213/20
See application file for complete search history.

(56) References Cited

U.S. PATENT DOCUMENTS

| | | | |
|---|---|---|---|
| 5,378,444 A | 1/1995 | Akita et al. |
| 9,722,281 B2 | 8/2017 | Magnes et al. |
| 9,905,874 B2 | 2/2018 | Magnes et al. |
| 2006/0204590 A1* | 9/2006 | Qian ................... C11D 3/3776 510/110 |

FOREIGN PATENT DOCUMENTS

| | | |
|---|---|---|
| EP | 0 277 292 | 8/1988 |
| EP | 0 684 067 | 11/1995 |
| WO | 00/61200 | 10/2000 |
| WO | 2012/130803 | 10/2012 |
| WO | 2017/081358 | 5/2017 |

OTHER PUBLICATIONS

Office Action and Search Report dated Sep. 14, 2022 in corresponding Chinese Application No. 202080039104.7 (with partial translation), 17 pages.
International Search Report for PCT/IL2020/050593 dated Sep. 9, 2020, 4 pages.
Written Opinion of the ISA for PCT/IL2020/050593 dated Sep. 9, 2020, 6 pages.

* cited by examiner

*Primary Examiner* — Timothy C Vanoy
(74) *Attorney, Agent, or Firm* — Nixon & Vanderhye PC

(57) ABSTRACT

The invention relates to a method for treating emergency spill or leak of halogen which is bromine or chlorine, comprising contacting an aqueous solution of quaternary ammonium halide with the halogen.

23 Claims, 4 Drawing Sheets

QUARTERNARY AMMONIUM HALIDES FOR TREATING HALOGEN CONTAMINATION

This application is the U.S. national phase of International Application No. PCT/IL2020/050593 filed May 27, 2020 which designated the U.S. and claims the benefit of U.S. Provisional Appln. No. 62/853,177 filed May 28, 2019, the entire contents of each of which are hereby incorporated by reference.

BACKGROUND OF THE INVENTION

Halogens are utilized for several industrial usages for instance flame retardants, biocides, drilling fluids and new applications such as energy storage. Elemental Bromine is liquid at room temperature with high vapor pressure. It is a strong oxidizer and accidental exposure to it without protection means may cause irritation, burns and poisoning depending on the exposure severity. In addition, bromine leakage poses an environmental hazard.

Elemental chlorine is gas at room temperature, having corrosive properties and is one of the most hazardous materials known. It has a greenish-yellow color with a pungent irritating odor and it is heavier than air, thus chlorine gas tends to settle in lower areas. An improper handling of chlorine gas can result in a major damage. According to EPA (US Environmental Protection Agency) reports, more than 1300 events of chlorine release occur each year, resulting in an average of 300 injuries and 27 deaths, more than any other chemical. Inhalation is the most dangerous route of chlorine gas exposure, causing severe lung damage which may lead to death. In the event of spill, chlorine expands rapidly, which makes such chlorine release a major concern.

To date, the procedure in the case of an emergency of a bromine leak includes a complex and time-consuming method comprising several different chemical substances working in parallel. The liquid bromine phase is often treated with $Ca(OH)_2$ and water while the gaseous bromine phase is treated with ammonia gas, which may cause a secondary ecological pollution risk caused by ammonia.

In the event of chlorine spill, water is sprayed towards the chlorine gas cloud to slow down its spreading and dilute its concentration.

The operating emergency team must include several well-trained members, in order to treat the gaseous and liquid phases of the spill simultaneously. The treatment involves close proximity to, and coming in contact with, the origin of the leak, which requires suited personal safety gear such as special protection suits, protection masks and respiratory aid.

Thus, there is a need for a facile and straightforward procedure, allowing a prompt response in case of an emergency, to prevent further spreading of halogens and the removal of the resultant waste in a safe and efficient manner.

SUMMARY OF THE INVENTION

The invention is primarily directed to a method for treating emergency spill or leak of halogen (bromine or chlorine), comprising contacting an aqueous solution of quaternary ammonium halide with the halogen. The quaternary ammonium halide is bromide or chloride and is selected from the group consisting of aliphatic and cyclic quaternary ammonium bromides or chlorides.

The method of the invention enables the rapid neutralization of the halogen and collection of the halogen neutralization product as complexed bromine in a form of liquid or solid mass, as shown in detail below.

DETAILED DESCRIPTION OF THE INVENTION

Since elemental bromine has high vapor pressure, a bromine leak demands a fast response time in order to contain the spill and prevent further contamination spreading. Thus, in one aspect, the present invention provides a method for isolating a bromine spill or leak, preventing said bromine from further evaporating and contaminating larger areas. Accordingly, the method of the invention can be applied to both liquid and/or gas phase bromine contamination by applying aqueous quaternary ammonium halide salt solution directly onto the bromine source sought to be isolated. According to the invention, the quaternary ammonium halide salt solution, when applied to elemental bromine ($Br_2$) source, causes the free bromine to become complexed to said salt. It is to be understood that complexed bromine does not present high vapor pressure and thus, the complexed bromine is considered safely contained.

In another aspect, the present invention provides a method for isolating/treating chlorine gas preventing said chlorine from further spreading and contaminating larger areas. Thus, the method of the invention can be applied to gas phase chlorine contamination by applying aqueous quaternary ammonium halide salt solution directly onto the chlorine source sought to be isolated. In some embodiments, the aqueous quaternary ammonium halide salt solution can be sprayed onto/in the direction of the incoming chlorine gas stream.

In certain embodiments, the aqueous quaternary ammonium halide salt solution of the invention is utilized for treating bromine vapor and preventing further spreading of the gas phase bromine. According to the invention, the aqueous quaternary ammonium halide salt solution is sprayed directly onto bromine gas phase/bromine vapor. Upon contact between the sprayed droplets of the quaternary ammonium halide salt solution with the bromine vapor, the bromine becomes complexed to said salt and remains in the liquid form, where the newly formed bromine-ammonium salt complex does not present high vapor pressure and thus, the complexed bromine is considered to be contained and does not further spread.

In other embodiments, the aqueous quaternary ammonium halide salt solution of the invention is utilized for treating a liquid bromine source. According to the invention, the aqueous quaternary ammonium halide salt solution is added to, poured or sprayed onto the liquid bromine source. Said addition of aqueous ammonium salt solution to liquid bromine results in the formation of two liquid phases; an upper aqueous phase (top phase), which consists mostly of water and residual amounts of quaternary ammonium salt and bromine; while the lower organic phase (bottom phase) comprises the majority of the bromine in the form of a bromine-quaternary ammonium salt complex. As can be understood, the lower phase which comprises the complexed bromine material is heavier than the water-based top phase, a fact which causes the heavier bromine-containing organic phase to become confined and isolated, that is, to eliminate the bromine-containing liquid/air interface.

According to the invention, upon addition of the quaternary ammonium halide salt solution to liquid bromine, the upper aqueous liquid surface exposed to air contains only residual amount of bromine and no bromine vapor is emitted after the salt addition and bromine complexation. The phase separation as described above occurs within seconds from the initial addition of the quaternary ammonium halide salt solution to the bromine liquid source, thereby providing a fast complexation and isolation of bromine.

The term "quaternary ammonium halide", as used herein, includes compounds composed of a cation in which nitrogen possesses a positive charge, and a counter halide anion. Nitrogen may assume a positive charge because it is attached to four carbon atoms, having the formula $R_1R_2R_3R_4N^+ \ X^-$ wherein $R_1$, $R_2$, $R_3$ and $R_4$ are independently selected from linear or branched $C_1$-$C_5$ alkyl groups and aryl groups, and $X^-$ indicates the counter anion which is halide, e.g., bromide or chloride, such as symmetrical quaternary ammonium halide salts wherein $R_1$, $R_2$, $R_3$ and $R_4$ are the same (e.g., tetra ethyl ammonium bromide (TEAB) and tetra n-butyl ammonium bromide (TBAB)). Quaternary ammonium halide salts in which the nitrogen forms part of a ring, e.g., five or six membered rings including aromatic rings are also useful in the present invention, i.e., pyridinium salts, such as 2-methyl-1-alkyl-pyridinium bromides, 2-methyl-1-alkyl-pyridinium chlorides, 3-methyl-1-alkyl-pyridinium bromides and 3-methyl-1-alkyl-pyridinium chlorides wherein the alkyl at position 1 of the ring is linear or branched C1-C5 group. For example, 3-methyl-1-n-butyl pyridinium bromide (3-MBPy) and 2-methyl-1-ethyl pyridinium bromide (2-MEPy). The synthesis of such pyridinium salts is described in U.S. Pat. Nos. 9,722,281 and 9,905,874. That is, the invention contemplates the use of aliphatic and cyclic quaternary ammonium halides, especially bromides.

In some additional embodiments, the concentration of the quaternary ammonium halide salt solution utilized as described herein above is not less than 30 wt. %, e.g., not less than 40 wt. %, and up to saturation (~90 wt. %), e.g., from 40 wt. % to 60 wt. %.

According to the invention, the concentration of the quaternary ammonium halide salt solution to be added to the liquid bromine, and more specifically the molar ratio between the ammonium salt and bromine affects the resultant lower phase physical properties. It was surprisingly found that the final physical state of the resultant lower phase (which consists of the complexed bromine) can be controlled to facilitate a safe removal of the complexed bromine from the location in which the contamination occurred to a safe bromine discarding area. It should be understood that the molar ratio mentioned above refers to the ratio of quaternary ammonium: bromine upon mixing the quaternary ammonium halide salt solution with the bromine solution sought to be treated and later discarded.

Therefore, in another aspect, the present invention provides a method of discarding bromine-containing waste which is formed due to a bromine leak or spill. According to the present invention, addition of quaternary ammonium salt solution such that the ratio of quaternary ammonium: bromine is in the range from 1:1 to about 1:8 will promote the formation of a solid phase, gel-like phase or liquid phase containing the complexed bromine within a few hours after the ammonium salt solution addition, depending on the quaternary ammonium salt utilized in the aqueous solution mixed with the bromine source. For example, utilizing tetra-ethyl ammonium bromide (TEAB) as the quaternary ammonium salt in the solution of the invention in a quaternary ammonium: bromine of between 1:1 to about 1:4 will produce a solid phase containing the complexed bromine, which can be easily removed from the original solution and collected by known methods e.g. filtration or manually. Said solid comprising the complexed bromine is characterized in being chemically and structurally stable for at least a 5 months period from the day the complexation of bromine took place.

In certain embodiments, recycling of the complexed bromine from either gel-like form or solid form can be achieved, and the bromine can be separated from the ammonium salt and reused.

In a further aspect, the present invention provides a method for isolating and/or passivating a liquid bromine source from the surroundings by forming a stable foam in the interface between the liquid bromine source and the surrounding area, said foam prevents bromine gas evaporation through its surface. The passivating foam of the invention is achieved by using an aqueous quaternary ammonium halide salt solution which comprises a foaming agent, and spraying said solution on the surface of the liquid bromine source sought to be passivated and isolated. The foam which is formed on the liquid bromine surface prevents the evaporation of bromine vapor from the bromine surface and therefore prevents further contamination of the surrounding atmosphere and environment by bromine vapor.

According to the present invention, the resultant foam undergoes hardening within a few hours and the solid phase formed can be safely discarded as disclosed herein above.

In some embodiments, the obtained foam and the bromine source phase form a single solid phase within several hours after the foam is applied on the liquid bromine source surface.

In some related embodiments, the foaming agent which is being utilized in the method described above is a surfactant being characterized as an aqueous film forming foam (AFFF). Said foaming agents are commonly used in firefighting applications. Accordingly, the foams which are being utilized in the present invention are either water-based foaming agents, containing hydrocarbon-based surfactants, for example, sodium alkyl sulfate, or alcohol resistant aqueous film forming foams (AR-AFFF). A non-limiting example of such alcohol resistant agent is FireAid-AR® 2000. Other foams which may be utilized in the present invention are C5-C10 short chain amphoteric surfactants, C5-C10 nonionic surfactant, anionic hydrocarbon surfactants and fluorinated surfactants.

In some other related embodiments, the concentration of said foaming agent in the quaternary ammonium salt solution is between 5 and 30 wt. %. In some other embodiments, the concentration of said foaming agent is between 5 and 15 wt. %.

The quaternary ammonium halide salt solutions of the invention are chemically stable and can be available for use on site. Thus, the present invention further provides halogen neutralization emergency system comprising sprayable or pourable aqueous solution of quaternary ammonium halide at a concentration of not less than 40 wt. %, that is, with the compositions described herein.

The system, for example, may be a portable apparatus comprising an aqueous quaternary ammonium halide salt solution, ready for use in case of an emergency. For example, a small scale system of 20 L aqueous quaternary ammonium salt solution, having a concentration of between about 40 wt. % to about 90 wt. % of ammonium salt can be assembled as a backpack, having a manual pump, for an easy addition of the aqueous quaternary ammonium salt of the invention to an exposed bromine source. In another example, a large-scale system comprising the above described solution of the invention can be installed on vehicles having the required format such as towing equipment or specialized lifting equipment, which can be utilized in more remote spill/leak origins.

Furthermore, fire extinguishing equipment can be converted and utilized under similar conditions as commonly used for suppressing fires, for example by filling a portable unit with quaternary ammonium salt solution having a concentration of between 40 wt. % and 90 wt. % and compressing said solution with air according to methods known to a person skilled in the art.

A specific aspect of the invention relates to a method of neutralizing an emergency leak of chlorine gas with the aid of an aqueous composition comprising:
quaternary ammonium bromide salt, e.g., aliphatic and cyclic quaternary ammonium bromide as previously defined; and
inorganic bromide source, e.g., alkali or alkaline earth metal bromide.

We have found that such a pair of bromide salts can be dissolved in water to create concentrated, slightly viscous yet readily pumpable/sprayable solutions, comprising, or consisting of: not less than 30 wt. %, e.g. >40 wt. %, >45 wt. % of one or more quaternary ammonium bromide salt(s); and
not less than 30 wt. %, e.g. >40 wt. %, >45 wt. % of one or more alkali or alkaline earth metal bromide such as sodium bromide, potassium bromide, calcium bromide or a mixture thereof.

The abovementioned solutions form an additional aspect of the invention, especially solutions made by dissolving in water a symmetrical quaternary ammonium bromide salt wherein $R_1$, $R_2$, $R_3$ and $R_4$ are the same, e.g., $R_1=R_2=R_3=R_4=$C1-C5 alkyl group (e.g., tetra ethyl ammonium bromide, tetra propyl ammonium bromide or tetra butyl ammonium bromide) with sodium bromide or calcium bromide.

Accordingly, the invention specifically provides halogen-neutralizing aqueous solution comprising:
from 30 to 60 wt. % (e.g., 40 to 60 wt. %) tetra alkyl ammonium bromide, wherein the alkyl is linear or branched $C_1$-$C_5$ alkyl; and
from 30 to 55 wt. % (e.g., 40 to 55 wt. %) sodium bromide or from 30 to 60 wt. % (e.g., 40 to 60 wt. %) calcium bromide.

One preferred aqueous solution comprises, or is consisted of:
from 30 to 60 wt. % (e.g., 40 to 60 wt. %) tetra ethyl ammonium bromide; and from 30 to 55 wt. % (e.g., 40 to 55 wt. %) sodium bromide.

One preferred aqueous solution comprises, or is consisted of:
from 30 to 60 wt. % (e.g., 40 to 60 wt. %) tetra ethyl ammonium bromide; and from 30 to 60 wt. % (e.g., 40 to 60 wt. %) calcium bromide.

Hereinafter we use the notation QABr/$M^{n+}$(Br)$_n$ (M=Na, M=K and n=1; or M=Ca and n=2) to indicate the "mixed" solutions. These solutions are conveniently prepared by combining saturated or nearly saturated solutions of the individual salts (for example, ~50 wt. % aqueous solution of tetra ethyl ammonium bromide, ~45 wt. % aqueous solution of sodium bromide and ~52 wt. % aqueous solution of calcium bromide can be used to prepare the "mixed" solutions). The density of the QABr/$M^{n+}$(Br)$_n$ solution is in the range from 1.2 to 1.7 g/cc. The solutions are stable against crystallization.

Experimental results reported below indicate that chlorine gas that was delivered to, and accumulated at, the bottom of a column, was effectively neutralized by spraying concentrated QABr/$M^{n+}$(Br)$_n$ solutions over the top of the column (that is, in a counterflow fashion). The experimental set-up is shown in FIG. 4 and described in detail below. A downstream located trap system, designed to balance pressure changes in the column and trap chlorine vapors escaping from the column, did not detect residual chlorine gas released from the column.

The added inorganic bromide source sustains the neutralizing action of the quaternary ammonium bromide. Chlorine is a stronger oxidizer than bromine:

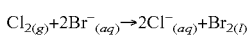

$$Cl_{2(g)}+2Br^-_{(aq)} \rightarrow 2Cl^-_{(aq)}+Br_{2(l)}$$

Once absorbed by the solution, chlorine is reduced by bromide ions. Chloride ions may therefore displace the bromide counter ion associated with the quaternary ammonium, resulting in the formation of the corresponding chloride, for example, tetra ethyl ammonium chloride. Experimental work conducted in support of this invention shows that tetra ethyl ammonium chloride is a poor complexing agent with respect to elemental chlorine. The benefit of adding an inorganic bromide source, such as sodium bromide or calcium bromide, resides in the supply of bromide ion for reduction of chlorine, enabling the quaternary ammonium to keep its bromide counter ions. The concomitantly generated elemental bromine can then strongly associate with the quaternary ammonium bromide. Displacement of bromide by chloride in the quaternary ammonium is inevitable to some extent, but this should not detract from the efficiency of the QABr/$M^{n+}$(Br)$_n$ pair because QACl works reasonably well as complexing agent for bromine molecules: our results show that tetra ethyl ammonium chloride is reasonably effective in coupling with the Bromine.

Accordingly, a specific aspect of the invention is a method of neutralizing an emergency leak of chlorine, e.g., from pipelines in chemical plants and other facilities where chlorine is supplied through pipelines to a site of its intended use (chemical reactor, etc.), the method comprises spraying the abovementioned QABr/$M^{n+}$(Br)$_n$ solution over the leak, and collecting chlorine neutralization product as complexed bromine in the form of a liquid or solid mass.

For example, a QABr/$M^{n+}$(Br)$_n$-based neutralization system may consist of sprayers positioned above chlorine pipelines to deliver the solution in response to detection of a chlorine leak. As noted above and shown in the experimental section below, concentrated QABr/$M^{n+}$(Br)$_n$ tested in similar fashion (spraying from top of column counterflow set-up onto chlorine gas) demonstrated high efficiency.

The invention also provides the use of an aqueous solution of quaternary ammonium halide having concentration of not less than 40 wt. % as halogen neutralization agent in case of emergency leak of the halogen, with the specific compositions described above. For the treatment of emergency leak of chlorine, the aqueous solution quaternary ammonium bromide preferably further comprises one or more alkali or alkaline earth metal bromides, with the specific compositions described in detail above.

The invention also provides a halogen neutralization emergency system, as mentioned before, comprising an aqueous solution of quaternary ammonium halide with concentration of not less than 40 wt. % in an instantly sprayable or pourable form, e.g., with the compositions described in detail above. When installed in a chlorine-neutralization emergency system, the sprayable aqueous solution further comprises one or more alkali or alkaline earth metal bromides, with the specific compositions described in detail above.

SHORT DESCRIPTION OF THE FIGURES

FIG. 1: 1A presents the wt. % change vs. time while 1B presents weight loss magnification of quaternary salts/bromine mixtures.

EXAMPLES

Example 1

Treatment of Bromine Vapor

Figure 1A:
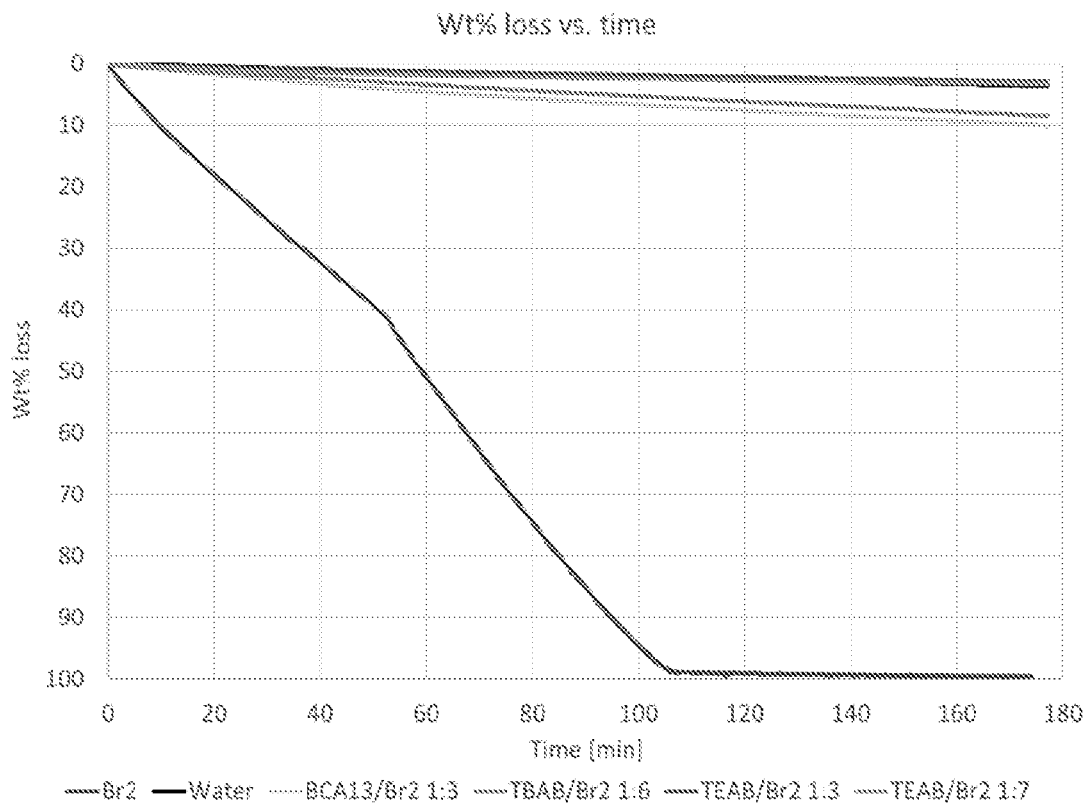

Two samples each of 10 gr liquid bromine ($Br_2$) were added to 250 ml glass bottles. The bottles were sealed, and $Br_2$ vapor was formed inside the bottles.

50 wt. % tetra-ethyl ammonium bromide (TEAB) aqueous solution was added to a small spraying flask.

The two sealed $Br_2$ containing bottles were opened and turned facing down vertically to release the heavy $Br_2$ vapor. Bottle number (1) was used as a reference, while bottle number (2) was treated as followed: about 3 ml of TEAB solution as described above was sprayed towards the opening of bottle number (2).

Results: reference bottle number (1) continued to release bromine vapor, while no vapor emission was observed from bottle number (2), which was sprayed with the TEAB solution and small brown drops were observed on the interior side of the bottle.

Example 2

Treatment of Bromine Spill

A) 42 gr of 50 wt. % 3-methyl-1-n-butyl pyridinium bromide (3-MBPy; also named BCA13) was added to a separating funnel containing 32 gr of liquid bromine (1:2 molar ratio). The two liquids were mixed via shaking the separating funnel and then kept still. Two phases were immediately formed, a top aqueous phase (slightly yellow) and a bottom organic phase (brown-red). The two phases were immediately collected (separately) and were analyzed utilizing HPLC and titration as follows:

Both phases were analyzed for $Br_2$ and 3-MBPy using iodometric titration (in which iodide oxidation was followed by titration with thiosulfate) and HPLC (HP 1100, Equipped with UV detector and CROMASYL C-18 column (2.1*250 mm), Agilent). The bottom phase (53.4 gr) was found to contain 37 wt. % 3-MBPy and 58 wt. % bromine. The top phase (20.4 gr) gave rise to a residual amount of 3000 ppm of 3-MBPy and 380 ppm of bromine.

B) Liquid bromine (160 gr) was introduced into a 1 L glass open vessel and bromine vapor was observed. Tetra-ethyl ammonium bromide (TEAB) aqueous solution (105 gr of 50 wt. % solution) was poured on the liquid bromine surface.

Results: two phases were immediately formed upon the addition of the TEAB solution and no bromine vapor was observed following the phase separation. The bottom phase was solidified after about two hours.

C) Liquid bromine (120 gr) was added to a 1 L glass open vessel and bromine vapor was observed. Tetra-butyl ammonium bromide (TBAB) aqueous solution (161 gr of 50 wt % solution) was poured on the liquid bromine surface.

Results: two phases were immediately formed upon the addition of the tetra-butyl ammonium bromide solution and no bromine vapor was observed following the phase separation. Two hours later, the bottom phase turned into a gel-like phase. The obtained gel-like phase was liquefied utilizing 40 gr of liquid bromine.

Example 3

Foam Passivation of Bromine Spill

A) Liquid bromine (50 gr) was added to a 1 L glass open vessel and bromine vapor was observed. A 25 gr solution containing 92 wt. % of TEAB solution of 50 wt. % tetra-ethyl ammonium bromide, and 8 wt. % of a foaming agent AR-AFFF FireAid-AR® 2000 solution was sprayed utilizing a pump spray on the liquid bromine surface.

Results: A foam was immediately formed on top of the bromine surface, covering the bromine-air interface, and no bromine vapor emission was observed.

An additional 30 gr liquid bromine was slowly added on top of the foam and did not cause any vapor release.

Several hours later, the entire bromine source and the surface-coating foam phase were solidified.

B) 50 gr of liquid bromine were poured into a 1 L glass open vessel and bromine vapor was observed. A 25 gr solution containing 50 wt. % 3-methyl-1-n-butyl pyridinium bromide (3-MBPy) solution (80 wt. %) and 8 wt. % of a foaming agent AR-AFFF FireAid-AR® 2000 was sprayed utilizing a pump spray on the liquid bromine surface.

Results: A foam was immediately formed on top of the bromine surface, covering the bromine-air interface, no bromine vapor emission was observed.

An additional 30 gr liquid bromine dripped on top of the foam and did not cause any vapor release.

C) 50 gr of liquid bromine were poured into a 1 L glass open vessel. The bottom of the vessel was covered with liquid bromine and bromine vapor was formed. 25 gr of 92 wt. % 2-MEPy solution (50 wt. % 2-methyl-1-ethyl pyridinium bromide, (2-MEPy) mixed with 8 wt. % of a foaming agent AR-AFFF FireAid-AR® 2000 solution was sprayed on the liquid bromine surface.

Results: A foam was immediately formed on top of the bromine surface, covering the bromine-air interface, and no bromine vapor emission was observed.

An additional 30 gr liquid bromine dripped on top of the foam and did not cause any vapor release.

Example 4

Collecting Treated Bromine Solids

Solid product of treated liquid bromine were obtained as described in examples 2B and 3. The solids were collected manually by spatula into a plastic container. No changes in the product was observed after a 3 months period.

Example 5

Collecting Treated Bromine Liquids

Liquid product of treated liquid bromine obtained as described in example 2C was collected manually by suction into a plastic container. No changes in the product was observed after a 3 months period.

Example 6

Evaporation Rate Measurements

The purpose of the study was to test the ability of quaternary ammonium salts added to liquid bromine to suppress release of bromine vapors. The study is based on monitoring a weight change for samples containing liquid bromine ($Br_2$; control), 3-MBPy/$Br_2$, TBAB/$Br_2$ and TEAB/$Br_2$ at various molar ratios as described in Table 1 herein below. The weight loss was measured under the same conditions as a reference.

A sample of (33 ml) was placed on a balance (0.01 g) and the weight was set to zero. The weight change was recorded every 5 seconds. The experiment took place under ambient conditions.

Figure 1B:
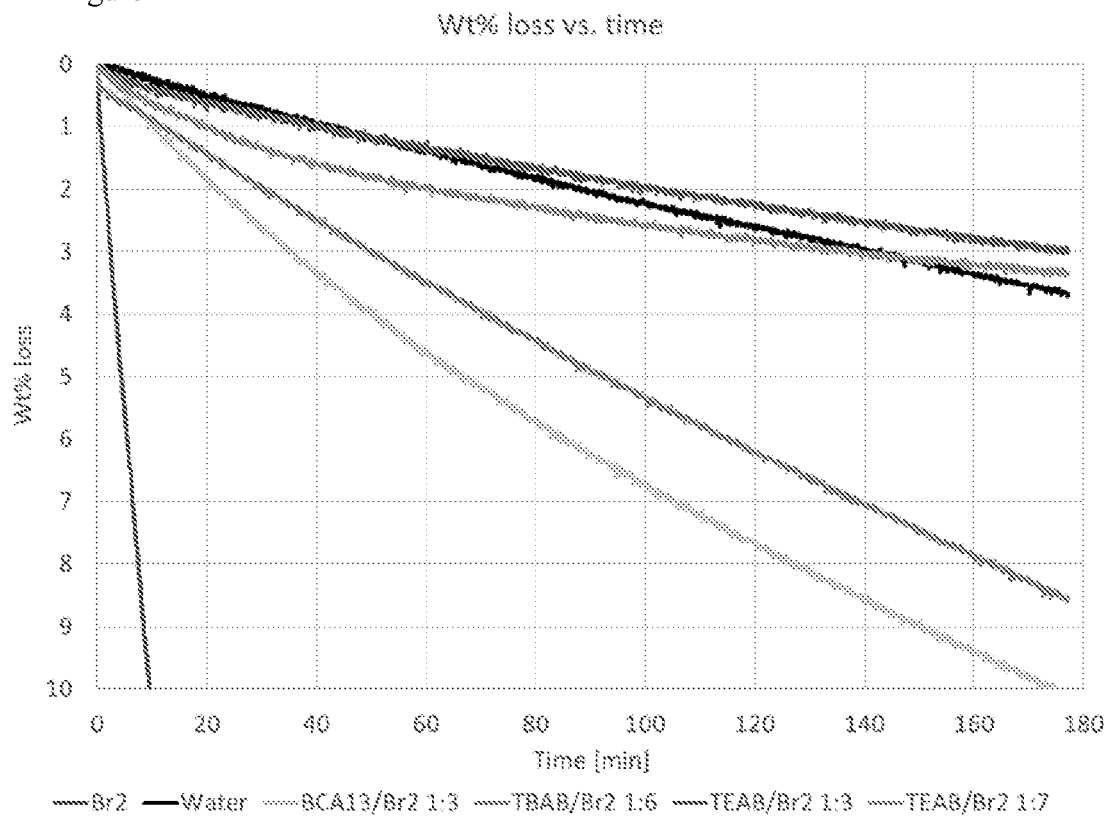
Figure 2A:
FIG. 2 depicts a $Cl_2$ capturing process as described in Example 8A. A is the starting point of the experiment, B is after the addition of 30 gr of chlorine, and D is the resultant phase separation at the end of the experiment.
Figure 2B:
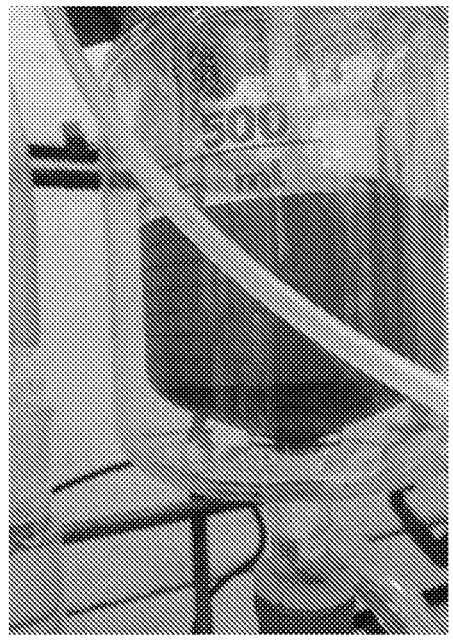
Figure 2C:
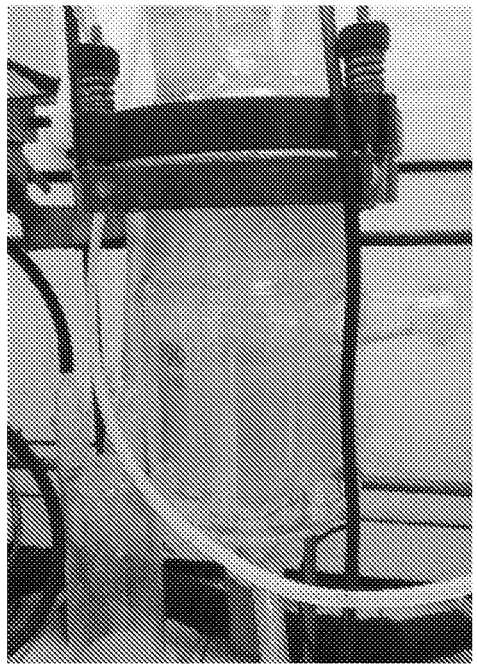
Figure 2D:
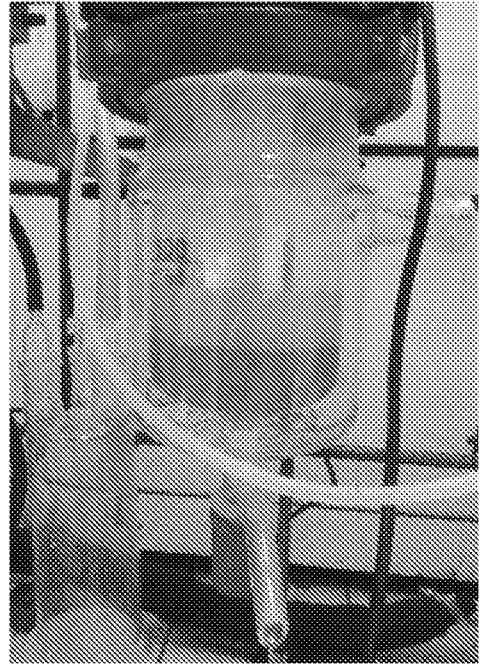
Figure 3A:
FIG. 3 depicts a $Cl_2$ capturing process as described in Example 8B. A is the starting point of the experiment, B is after the addition of 50 gr of chlorine, C is after the addition of 93 gr of chlorine and D is after the addition of 147 gr of chlorine.
Figure 3B:
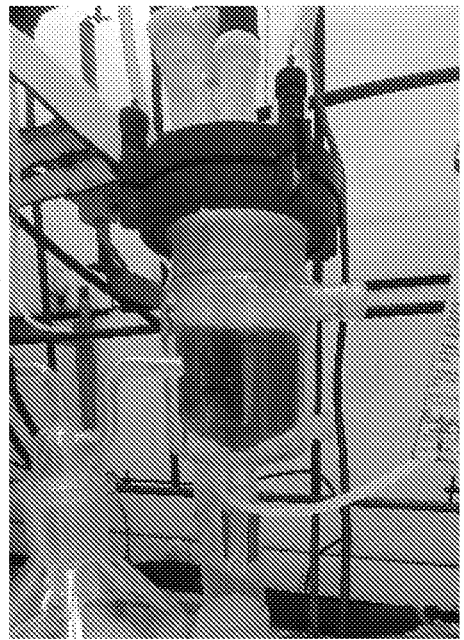
Figure 3C:
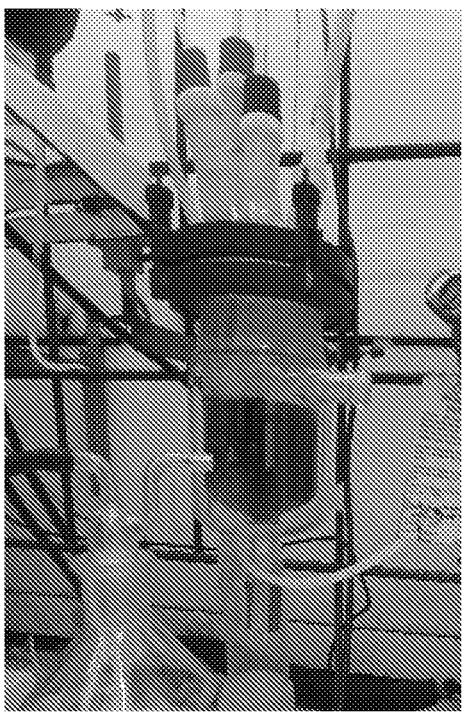
Figure 3D:
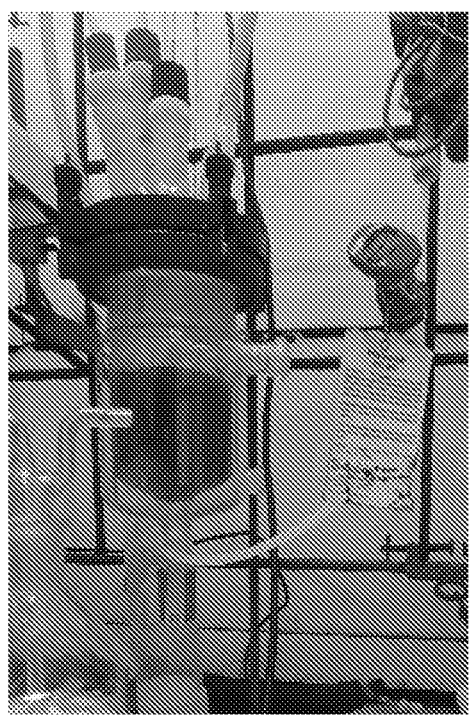

Results: As presented in FIGS. 1A and 1B and Table 1 herein below, it was demonstrated that even upon addition of a small amount of quaternary ammonium bromide to bromine a significant reduction of bromine evaporation occurs. A weight loss rate of 50.04 gr/hr was measured for liquid bromine by itself, and was reduced to 3.96 gr/hr in a system comprising 3-MBPy and bromine in a molar ratio of 1:3. Further weight loss rate reduction was achieved utilizing TEAB with the same molar ratio (1:3), yielding a minimal weight loss of 1.08 gr/hr.

TABLE 1

| # | Sample composition | ratio | weight loss rate [gr/hr] |
|---|---|---|---|
| 1 | water | — | 1.44 |
| 2 | Elemental Bromine | — | 50.04 |
| 3 | 3-MBPy/Br2 | 1:3 | 3.96 |
| 4 | TBAB/Br2 | 1:6 | 3.24 |
| 5 | TEAB/Br2 | 1:3 | 1.08 |
| 6 | TEAB/Br2 | 1:7 | 1.8 |

Example 7

Effect of Quaternary Ammonium Salt on the Physical Form of the Complexed Bromine Different quaternary ammonium salts were tested to determine their ability to complex bromine in different molar ratios. Solutions of 3-methyl-1-n-butyl pyridinium bromide (3-MBPy), tetra-butyl ammonium bromide (TBAB) and tetra-ethyl ammonium bromide (TEAB) [50 wt. % solution, total of 0.25 mole quaternary ammonium salt] were mixed with liquid bromine in varied weights of 40, 80, 120, 160 and 200 gr in a glass container in a molar ratio as described in Table 2. The resultant lower phase obtained after the mixing was characterized according to the physical state and whether bromine vapor was observed after the complexation occurred.

TABLE 2

| Quaternary ammonium:bromine | 3-MBPy | TBAB | TEAB |
|---|---|---|---|
| 1:1 | Liquid | Liquid | Solid |
| 1:2 | Liquid | Gel - like | Solid |
| 1:3 | Liquid | Gel - like | Solid |
| 1:4 | Liquid | Gel - like | Solid |
| 1:5 | Liquid (slight bromine emission) | Liquid (slight bromine emission) | Gel - like (slight bromine emission) |
| 1:6 | Liquid (slight bromine emission) | Liquid (slight bromine emission) | Liquid (slight bromine emission) |

As can be seen from Table 2, the physical form of the complexed bromine depends not only on the kind of quaternary ammonium salt utilized for its complexation but also might be dependent on the molar ratio between said quaternary ammonium salt and bromine. Furthermore, it can be seen that for 3-MBPy, TBAB and TEAB no bromine evaporation was observed up to a molar ratio of 1:4 Quaternary ammonium: bromine.

Example 8

Neutralization of Chlorine ($Cl_2$) Gas with Quaternary Ammonium Bromide Alone and with Quaternary Ammonium Bromide/NaBr A. 460 gr 50 wt. % of 3-MBPy solution was inserted into a glass vessel. The glass vessel was vented, the solution was stirred and the emissions were trapped in a 20 wt. % NaOH trap.

$Cl_2$ gas was bubbled into the vessel. $Cl_2$ gas addition was carried out from a chlorine gas compressed tank, which was controlled and recorded using a semi-analytical balance. Phase separation was observed after 30 gr $Cl_2$ addition as can be observed in FIG. 2. The solution color became brighter during the $Cl_2$ addition progress.

A total of 2 mole (142 gr) chlorine gas were captured in the described 3-MBPy solution.

B. 460 gr 50 wt. % of 3-MBPy solution was added into a glass vessel. 155 gr NaBr was added into the solution. The glass vessel was vented, the solution was stirred and the emissions were trapped in a 26 wt. % NaOH trap.

$Cl_2$ gas was bubbled into the vessel (for a duration of 105 minutes). $Cl_2$ gas addition was carried out from a chlorine gas compressed tank, which was controlled and recorded using a semi-analytical balance. The solution's color became darker during the $Cl_2$ addition progress as can be observed in FIG. 3. The chlorine gas addition was stopped upon observed gas emission in the trap.

A total of 2.45 mole (174 gr) chlorine gas were captured in the described 3-MBPy:NaBr solution. The reaction was exothermic and the temperature reached 70.8° C. following the addition of 80 gr chlorine. Further addition of chlorine did not cause a further increase in temperature.

Examples 9 to 12

Figure 4:
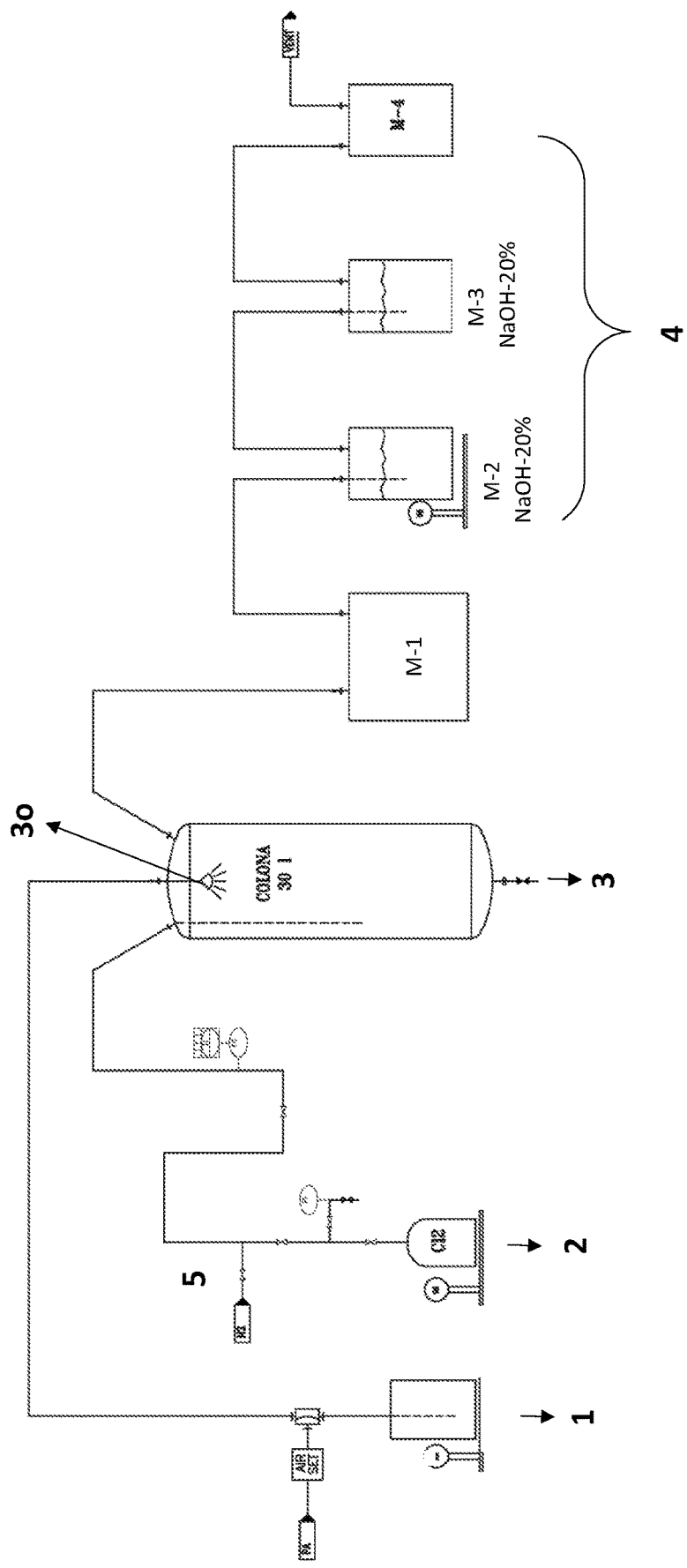
FIG. 4 illustrates an experimental set-up used for chlorine neutralization.

Eliminating $Cl_2$ Gas Release by Counter Spraying of a Treatment Solution of Quaternary Ammonium Bromide/Inorganic Bromide The experimental set-up used for the next set of Examples is shown in FIG. 4. The experimental set-up consists of three major parts: feeding sources (1) and (2), a reaction chamber (3) and a gas trapping system (4). From the feeding sources, controlled quantities of $Cl_2$ gas (2) and the treatment solution consisting of quaternary ammonium bromide and inorganic bromide salt (1) are delivered separately into the reaction chamber. The $Cl_2$ inlet is located at the bottom part of the reaction chamber (column 3, which is a 30 L closed glass vessel). The solution is fed from tank (1) into column (3) in a counterflow fashion, by spraying through a nozzle (3o) positioned at the center of the top section of column (3).

A chemical reaction between the $Cl_2$ gas and the reaction solution takes place in the interior of column (3): $Cl_2$ reduction by the bromide ion, and complexation of the elemental bromine formed by the quaternary ammonium halide. The atmospheric pressure inside the reaction chamber is balanced by permitting two-direction gas flow through the trapping system (4). The trapping system consists of three trapping vessels (M1, M2 and M3) connected in series from one end of the reaction chamber (column 3) to the exhaust. The first trap M1 consists of an empty vessel and is used to prevent the flow of trap solution into the reaction chamber (column 3) when a negative pressure is built up in the column. The other two traps (M2 and M3) are filled with sodium hydroxide solution (20-25 wt. %) to collect and neutralize $Cl_2$ or $Br_2$ gas escaping from the column (3). There is an activated carbon trap at the end (M4).

The experimental set-up shown in FIG. 4 was used to perform a series of tests, the conditions of which are tabulated in Table 3 below. Briefly, a quantity of $Cl_2$ gas (indicated in Table 3, column A) was released from cylinder (2) during a time period (indicated in Table 3, column B) through a bottom joint of an empty 30 L closed glass vessel (column 3). When the interior of the vessel started acquiring yellow color at the bottom, indicating accumulation of chlorine gas, a treatment solution consisting of TEAB and inorganic bromide salt was pumped from tank (1) and sprayed through a nozzle located at the top part of the vessel. The volume of the TEAB/M$^{n+}$Br$_n$ solution supplied to the reaction vessel and its composition are indicated in Table 3, column C).

The reaction between the $Cl_2$ gas and the treatment solution TEAB/M$^{n+}$Br$_n$ led to formation of a red product, either in a solid or liquid form (product phase is indicated in Table 3, column D), and consequently, internal negative pressure was created. As a result, the 1st trap (M1) was filled with sodium hydroxide solution drawn from the 2nd and 3rd traps (M2 and M3, respectively).

Table 3 below summarizes the conditions of each experiment and the product formed.

consisting of TEAB/M$^{n+}$Br$_n$, and its conversion into harmless product which is readily removable from the reaction vessel.

Example 13 (Comparative)

Neutralization of Chlorine ($Cl_2$) Gas

The experimental set-up shown in FIG. 4 and described in detail above was used for the experiment. $Cl_2$ gas (107 gr) was released (2) during a period of 5 minutes through a bottom joint of an empty 30 L closed glass vessel (3). During the first five minutes air bubbles were observed inside the sodium hydroxide trap M2, as $Cl_2$ pushed out the air in the glass vessel (3). During the next nine minutes the color of the sodium hydroxide solution in the first sodium hydroxide trap (M2) changed to yellowish green. No bubbles were observed and no color change was visible in the 3rd trap (M3). After shutting down the $Cl_2$ flow, $N_2$ gas (5) was purged into the glass vessel (3) to wash out any remaining $Cl_2$ gas inside the reaction vessel.

At the end of experiment a positive weight change of 97.7 gr and 3.8 gr were determined in the first NaOH trap (M2) and second NaOH (M3) trap, respectively.

Example 14

Neutralization of Chlorine ($Cl_2$) Gas 20 gr $CaBr_2$ powder were dissolved in 105 gr of TEAB aqueous solution (50 wt. %) inside a 200 ml glass vessel (connected to a NaOH trap). $Cl_2$ gas (32 gr) from pressure regulated tank was bubbled into the solution at a flow rate of 0.47 gr/min. The temperature during the experiment was in the range of 30-40° C. After 68 minutes, emission of $Cl_2$ gas was observed in the NaOH trap, indicating the exhaustion of the TEAB/$CaBr_2$ reagent. The process was stopped, and the final product solution was separated into two phases—an upper aqueous yellow phase and a reddish organic phase at the bottom, indicating accumulation of elemental bromine in the organic phase. The organic phase solidified after 1 hour.

Example 15 (of the Invention) and 16 (Comparative)

Testing Quaternary Ammonium Chloride in Complexation of Halogen

The quaternary ammonium chloride chosen for the experiments was tetra ethyl ammonium chloride (TEACl).

TABLE 3

| Example | A $Cl_{2(g)}$ (gr) | B [min] | C [Treatment solution composition] | D Product phase |
|---|---|---|---|---|
| 9 | 118 | 4 | 1.2 L: 840 gr TEAB (50 wt. %) + 916 gr NaBr solution (45 wt. %) | Solid |
| 10 | 155 | 10 | 5 L: 2940 gr TEAB (50 wt. %) + 3206 gr NaBr solution (45 wt. %) + 206 gr NaBr(s) | Mostly Liquid |
| 11 | 108 | 4:30 | 3 L: 1680 gr TEAB (50 wt. %) + 1538 gr CaBr2 (52 wt. %) | Solid |
| 12 | 245 | 3 | 1.2 L: 840 gr TEAB (50 wt. %) + 769.2 gr CaBr2 (52 wt. %) | Solid |

No residual of $Cl_2$ gas was detected (<10 ppm) in the 1$^{st}$ (M1), 2$^{nd}$ (M2) and 3$^{rd}$ (M3) traps, indicating complete absorption of the chlorine gas by the treatment solution Bromine complexation was investigated (Example 15). 0.4 mole of liquid bromine (64 gr) were mixed with 0.1 mole of TEACl (50 wt. %) solution (36 gr). 3 equivalents (48 gr)

of Bromine were complexed by the TEACl solution, the 4th equivalent addition led to the appearance of light bromine vapor emission.

Chlorine complexation was investigated (Example 16). 10 gram $Cl_2$ gas was bubbled into 108 gr TEACl solution (50 wt. %). The $Cl_2$ emission was collected by sodium hydroxide solution (25 wt. %) trap. No weight change was observed in the TEACL solution, indicating that $Cl_2$ was entirely adsorbed by the trap (namely, no $Cl_2$ was captured by TEACl).

The invention claimed is:

1. A method for treating emergency spill or leak of halogen which is bromine or chlorine, comprising contacting an aqueous solution of quaternary ammonium halide with the halogen,
    wherein the quaternary ammonium halide is selected from the group consisting of aliphatic and cyclic quaternary ammonium bromides or chlorides,
    wherein the aliphatic quaternary ammonium bromide is of the formula $R_1R_2R_3R_4N^+Br^-$, wherein $R_1$, $R_2$, $R_3$ and $R_4$ are independently selected from linear or branched $C_1$-$C_5$ alkyl,
    wherein the $R_1R_2R_3R_4N^+Br^-$ is symmetrical quaternary ammonium bromide, such that $R_1$, $R_2$, $R_3$, and $R_4$ are the same,
    wherein the quaternary ammonium bromide is tetra ethyl ammonium bromide, tetra propyl ammonium bromide, or tetra butyl ammonium bromide, and
    wherein the cyclic quaternary ammonium bromide or chloride is selected from the group consisting of 2-methyl-1-alkyl-pyridinium bromides, 2-methyl-1-alkyl-pyridinium chlorides, 3-methyl-1-alkyl-pyridinium bromides and 3-methyl-1-alkyl-pyridinium chlorides wherein the alkyl at position 1 of the ring is linear or branched $C_1$-$C_5$ group.

2. The method of claim 1, wherein the 2-methyl-1-alkyl-pyridinium bromide is 2-methyl-1-ethyl pyridinium bromide (2-MEPy) and the 3-methyl-1-alkyl-pyridinium bromide is 3-methyl-1-n-butyl pyridinium bromide (3-MBPy).

3. The method of claim 1, wherein the halogen is bromine.

4. The method of claim 1, wherein the bromine is liquid bromine.

5. The method of claim 4, wherein the aqueous solution of the quaternary ammonium halide comprises a foaming agent, to form a foam on top of the liquid bromine.

6. The method of claim 5, wherein the foaming agent is an aqueous film forming foam (AFFF) agent.

7. The method of claim 5, wherein the quaternary ammonium halide is tetra ethyl ammonium bromide and the foaming agent is an aqueous film forming foam (AFFF) agent.

8. The method of claim 1, wherein the bromine is bromine gas.

9. The method of claim 1, comprising collecting halogen neutralization product as complexed bromine in a form of liquid or solid mass.

10. The method of claim 1, wherein the halogen is chlorine gas, and wherein the aqueous solution of quaternary ammonium bromide further comprises one or more alkali or alkaline earth metal bromides.

11. The method of claim 10, wherein the aqueous solution comprises not less than 40 wt. % of quaternary ammonium bromide and not less than 40 wt. % alkali or alkaline earth metal bromide.

12. The method of claim 11, wherein the aqueous solution comprises:
    a symmetrical quaternary ammonium bromide of the formula $R_1R_2R_3R_4N^+Br^-$ wherein $R_1$, $R_2$, $R_3$ and $R_4$ are the same C1-C5 alkyl groups; and sodium bromide or calcium bromide.

13. The method of claim 12, wherein the aqueous solution comprises tetra ethyl ammonium bromide and calcium bromide.

14. The method of claim 11, wherein the aqueous solution comprises tetra ethyl ammonium bromide, tetra propyl ammonium bromide or tetra butyl ammonium bromide.

15. The method of claim 14, wherein the aqueous solution comprises tetra ethyl ammonium bromide.

16. Halogen-neutralizing aqueous solution comprising:
    from 30 to 60 wt. % tetra alkyl ammonium bromide, wherein the alkyl is linear or branched $C_1$-$C_5$ alkyl; and
    from 30 to 55 wt. % sodium bromide or from 30 to 60 wt. % calcium bromide.

17. The halogen-neutralizing aqueous solution of claim 16, comprising:
    from 40 to 60 wt. % tetra alkyl ammonium bromide; and
    from 40 to 55 wt. % sodium bromide or from 40 to 60 wt. % calcium bromide.

18. The halogen-neutralizing aqueous solution of claim 17, comprising:
    from 40 to 60 wt. % tetra ethyl ammonium bromide; and
    from 40 to 60 wt. % calcium bromide.

19. The halogen-neutralizing aqueous solution of claim 16, wherein the tetra alkyl ammonium bromide is tetra ethyl ammonium bromide.

20. Use of an aqueous solution of quaternary ammonium halide with concentration of not less than 40 wt. % as halogen neutralization agent in case of emergency leak of the halogen, wherein the halide is bromide, and wherein the aqueous solution of quaternary ammonium bromide further comprises one or more alkali or alkaline earth metal bromides.

21. The use of claim 20, wherein the quaternary ammonium halide is tetra ethyl ammonium bromide, and wherein the alkaline earth metal bromide is calcium bromide.

22. Chlorine neutralization emergency system comprising an aqueous solution of quaternary ammonium halide with concentration of not less than 40 wt. % in an instantly sprayable or pourable form, wherein the halide is bromide, wherein the aqueous solution of quaternary ammonium bromide further comprises one or more alkali or alkaline earth metal bromides.

23. The chlorine neutralization emergency system of claim 22, wherein the quaternary ammonium halide is tetra ethyl ammonium bromide, and wherein the alkaline earth metal bromide is calcium bromide.

* * * * *